United States Patent [19]

Reel et al.

[11] Patent Number: 5,624,937
[45] Date of Patent: Apr. 29, 1997

[54] CHEMICAL COMPOUNDS AS INHIBITORS OF AMYLOID BETA PROTEIN PRODUCTION

[75] Inventors: Jon K. Reel, Carmel; Richard L. Simon; Celia A. Whitesitt, both of Greenwood, all of Ind.

[73] Assignee: Eli Lilly and Company, Indianapolis, Ind.

[21] Appl. No.: 397,466

[22] Filed: Mar. 2, 1995

[51] Int. Cl.$^6$ .......................... A61K 31/47; A61K 31/44; C07D 215/227; C07D 215/36
[52] U.S. Cl. .......... 514/312; 514/247; 514/351; 514/367; 514/376; 514/395; 514/586; 544/239; 546/153; 546/157; 546/300; 548/221; 548/222; 548/306.4; 564/27; 564/29
[58] Field of Search ..................... 546/153, 157, 546/300; 514/312, 351, 247, 367, 376, 395, 586; 564/27, 29; 544/239; 548/306.4, 221, 222

[56] References Cited

PUBLICATIONS

Kempter G, Beerbalk HD (1983) Wiss. Z. Paedagog. Hochsch. "Karl Liebnecht" Potsdam 27(1) 101–20.
Haan J, Maat–Schieman ML, Roos RA (1994) Dementia 5 (3–4) 210–3. (Abstract).

U.S. application No. 08/398188, Heinz, et al., filed Mar. 2, 1995 (co–pending application).

Primary Examiner—C. Warren Ivy
Assistant Examiner—Evelyn Huang
Attorney, Agent, or Firm—Arleen Palmberg; Martin A. Hay; David E. Boone

[57] ABSTRACT

A compound of the formula I in which

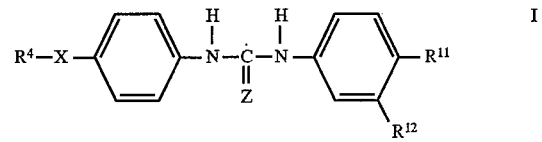

Z is O or S;
$R^{11}$ is a halogen atom;
$R^{12}$ is a halogen atom or a trifluoromethyl group; and
X is S, SO, SO$_2$, O or NH;
$R^4$ is naphthyl, quinolinyl, benzimidazolyl, pyridyl, pyradazinyl, benzoxazolyl or benzothiazolyl, unsubstituted or substituted by one or two substituents selected from a halogen atom, (1–4C)alkyl, (1–4C)alkoxy, nitro, (1–4C)alkoxycarbonyl, halo(1–4C)alkyl, and phenyl;
or a pharmaceutically acceptable salt thereof.

The compounds are useful as inhibitors of amyloid beta-protein production.

12 Claims, No Drawings

CHEMICAL COMPOUNDS AS INHIBITORS OF AMYLOID BETA PROTEIN PRODUCTION

The present invention relates to novel urea derivatives useful as inhibitors of amyloid beta-protein production, to processes for their preparation and to pharmaceutical compositions containing them.

Amyloid beta-protein (Aβ) is a neurotoxic polypeptide containing about 40 amino acid residues. It is produced by enzymatic cleavage of a larger precursor protein, beta-amyloid precursor protein, which is encoded by a gene on human chromosome 21, and is found in the brains of individuals suffering from Alzheimer's disease in deposits known as senile plaques. It is now widely believed that Aβ is involved in the pathogenesis of Alzheimer's disease, and substantial efforts are being made to find ways of intervening in this involvement, for example by inhibiting the production of Aβ.

It has now been found that certain novel urea derivatives are capable of inhibiting the production of Aβ in cells.

The present invention provides a compound of the formula

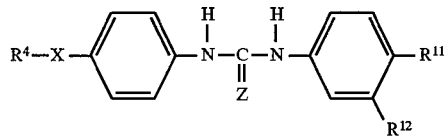

in which
Z is O or S;
$R^{11}$ is a halogen atom;
$R^{12}$ is a halogen atom or a trifluoromethyl group;
X is S, SO, $SO_2$, O or NH; and
$R^4$ is naphthyl, quinolinyl, benzimidazolyl, pyridyl, pyridazinyl, benzoxazolyl or benzothiazolyl, unsubstituted or substituted by one or two substituents selected from a halogen atom, (1–4C)alkyl, (1–4C)alkoxy, nitro, (1–4C) alkoxycarbonyl, halo(1–4C)alkyl, and phenyl; or a pharmaceutically acceptable salt thereof.

It has been found that urea derivatives of formula I are capable of inhibiting the production of Aβ in whole cells. Accordingly, it is believed that these compounds will be capable of inhibiting the production of Aβ generally in biological systems, and will be capable of inhibiting the accumulation of Aβ in senile plaques in a warm blooded mammal, such as man. The urea derivatives should therefore be capable of protecting a warm blooded mammal, such as man, from the progression of Alzheimer's disease.

According to another aspect, therefore, the present invention provides a method of inhibiting the accumulation of Aβ in senile plaques in a warm blooded mammal, which comprises administering an effective amount of a compound of formula I, or a pharmaceutically acceptable salt thereof.

According to yet another aspect, the present invention provides a method of protecting a warm blooded mammal from the progression of Alzheimer's disease, which comprises administering an effective amount of a compound of formula I, or a pharmaceutically acceptable salt thereof.

According to yet another aspect, the present invention provides a method of protecting a warm blooded mammal from the progression of Alzheimer's disease, which comprises administering an effective amount of a compound of formula I, or a pharmaceutically acceptable salt thereof.

The present invention also provides the use of a compound of formula I, or a pharmaceutically acceptable salt thereof, in the manufacture of a medicament for the treatment of Alzheimer's disease.

Examples of values for $R^{11}$ or $R^{12}$ when either represents a halogen atom are fluorine, chlorine or bromine.

Preferably $R^{11}$ is chlorine and $R^{12}$ is chlorine or trifluoromethyl.

Examples of a halogen atom substituent on $R^4$ are fluorine, chlorine and bromine.

Examples of a (1–4C)alkyl substituent on $R^4$ are methyl, ethyl, propyl, isopropyl, butyl, isobutyl and tert-butyl.

Examples of a (1–4C)alkoxy substituent on $R^4$ group are methoxy and ethoxy.

An example of a halo(1–4C) alkyl substituent $R^4$ is trifluoromethyl.

An example of a (1–4C) alkoxycarbonyl substituent on $R^4$ is ethoxycarbonyl.

$R^4$ is preferably unsubstituted or substituted naphth-1-yl, naphth-2-yl, quinolin-2-yl, quinolin-4-yl, quinolin-6-yl, benzimidazol-2-yl, benzoxazol-2-yl, benzothiazol-2-yl, pyridin-2-yl or pyridazin-3-yl.

Examples of particular values for $R^4$ are naphth-1-yl, naphth-2-yl, quinolin-2-yl, 6-chloroquinolin-2-yl, methoxyquinolin-2-yl, 5-nitroquinolin-6-yl, 4-ethoxycarbonylquinolin-2-yl, 4-phenylquinolin-2-yl, 7-trifluoromethylquinolin-4-yl, quinolin-4-yl, benzimidazol-2yl, benzoxazol-2-yl, benzothiazol-2-yl, 5-chlorobenzothiazol-2-yl, 6-phenylpyrazin-3-yl or pyridin-2-yl.

X preferably represents S.
Z preferably represents S.
A particularly preferred group of compounds of formula I is that in which
Z is O or S;
$R^{11}$ is a chlorine atom;
$R^{12}$ is a chlorine atom or a trifluoromethyl group;
X is S, SO, $SO_2$, O or NH; and
$R^4$ is naphth-1-yl, naphth-2-yl, quinolin-2-yl, 6-chloroquinolin-2-yl, 6-methoxyquinolin-2-yl, 5-nitroquinolin-6-yl, 4-ethoxycarbonylquinolin-2-yl, 4-phenylquinolin-2-yl, 7-trifluoromethylquinolin-4-yl, quinolin-4-yl, benzimidazol-2-yl, benzoxazol-2-yl, benzothiazol-2-yl, 5-chlorobenzothiazol-2-yl, 6-phenylpyrazin-3-yl or pyridin-2yl.

A particularly preferred compound is 1-[4-(2-quinolyl)-thiophenyl]-3-(4-chloro-3-trifluoromethylphenyl)thiourea.

The term "pharmaceutically acceptable salt" refers to a salt of a compound of formula I which is substantially non-toxic to living organisms. Typical pharmaceutically acceptable salts include those salts prepared by reaction of a compound of formula I with a pharmaceutically acceptable mineral acid or organic acid, or a pharmaceutically acceptable mineral or organic base, depending on the types of groups present in the compound of the formula I.

Examples of pharmaceutically acceptable mineral acids which may be used to prepare pharmaceutically acceptable salts include hydrochloric acid, phosphoric acid, sulfuric acid, hydrobromic acid, hydriodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkynic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroxide, hydrofluoride, acetate, propionate, ormate, oxalate, citrate, lactate, p-toluenesulfonate, methanesulfonate, maleate, and the like.

The compounds of formula I may be prepared by reacting a compound of formula III

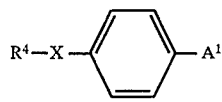

with a compound of formula IV

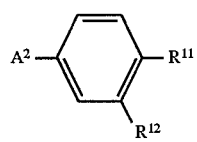

in which one of $A^1$ and $A^2$ represents $NH_2$ and the other represents —NCZ or —NHC(Z)$Z^a$ in which $Z^a$ is a leaving atom or group, and Z, X, $R^4$, $R^{11}$ and $R^{12}$ have any of the meanings given in claim 1.

whereafter, if desired, forming a pharmaceutically acceptable salt.

$Z^a$ may represent, for example, an amine group such as —$NH_2$, an alkylthio group such as methylthio, an aryloxy group such as phenoxy, or an acetylene group, such as a (2–10C) alk-1-ynyl group.

When the other of $A^1$ and $A^2$ represents —NCZ, the reaction is conveniently performed in the presence of solvent such as water, an ether, for example tetrahydrofuran, a halogenated hydrocarbon, such as dichloromethane, or an amide such as dimethylformamide. The temperature at which the reaction is conducted is conveniently in the range of from 0° to 150° C. Optionally, the reaction may be performed in the presence of a base, for example a tertiary amine, such as dimethylaminopyridine, or an alkali metal carbonate such as potassium carbonate.

When the other of $A^1$ and $A^2$ represent —NHC(Z)$Z^a$ in which $Z^a$ represents an acetylene group, the reaction is preferably performed in the presence of an alkali metal amide, such as sodium amide. The reaction is conveniently performed at a temperature in the range of from 0° to 50° C.

When the other of $A^1$ and $A^2$ represents —NHC(Z)$Z^a$ in which $Z^a$ represents a leaving atom or group other than an acetylene group, the reaction is conveniently performed at a temperature in the range of from 0° to 150° C. Suitable solvents include acetic acid, esters, such as ethyl acetate and ethers such as tetahydrofuran.

The compounds of formula III and IV in which the other of $A^1$ and $A^2$ represents —NC or —NCH(Z)$Z^a$ may be prepared by methods known in the art from the corresponding compounds of formula III or IV respectively in which $A^1$ or $A^2$ respectively represents —$NH_2$. For example, a compound of formula III or IV in which $A^1$ or $A^2$ represents —$NH_2$ may be converted into the corresponding compound in which $A^1$ or $A^2$ represents —NCZ by reaction with phosgene, and into a corresponding compound in which $A^1$ or $A^2$ represents —$NHCONH_2$ by reaction with an alkali metal cyanate, such as sodium cyanate.

The ability of a compound to inhibit the production of Aβ in a biological system may be demonstrated by the following test method.

Two cell lines (human kidney cell line 293 and Chinese hamster ovary cell line CHO) were stably transfected with the gene for APP-751 containing the double mutation $Lys_{651}$-$Met_{652}$ to $Asn_{651}$-$Leu_{652}$ (APP-751 numbering) commonly called the Swedish mutation using the method described in Citron et al., (1992) Nature 360: 672–674. The transfected cell lines were designated as 293 751 SWE and CHO 751 SWE, and were plated in Corning 96 well plates at 2.5×10$^4$ or 1×10$^4$ cells per well respectively in Dulbecco's minimal essential media plus 10% fetal bovine serum. Following overnight incubation at 37° C. in an incubator equilibrated with 10% carbon dioxide ($CO_2$), the media were removed and replaced with 200 μL per well of media containing a test compound. After a two hour pretreatment period, the media were again removed and replaced with fresh media containing the test compound and the cells were incubated for an additional two hours.

Test compound stocks were prepared in DMSO such that at the final concentration used in the treatment, the concentration of DMSO did no exceed 0.5%. After treatment, plates were centrifuged in a Beckman GPR at 1200 rpm for five minutes at room temperature to pellet cellular debris from the conditioned media. From each well, 100μL of conditioned media were transferred into an ELISA plate precoated with antibody 266 against βAP-13-28 (Seubert et al, supra.) and stored at 4° C. overnight. An ELISA assay employing labeled antibody 6C6 (against βAP-1-16) was run the next day to measure the amount of Aβ produced.

Cytotoxic effects of the test compounds were measured by a modification of the method of Hansen et al., (1989) J. Immun. Meth. 119: 203–210. To the cells remaining in the tissue culture plate, was added 25 μL of a 3,(4,5-dimethylthiazol-2-yl)2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% DMF, pH 4.7). Complete extraction was achieved by overnight shaking at room temperature. The difference in the $OD_{562\ nm}$ and the $OD_{650\ nm}$ was measured in a Molecular Devices $UV_{max}$ microplate reader as an indicator of the cellular viability.

The results of the Aβ ELISA were fit to a standard curve and expressed as ng/mL Aβ peptide. In order to normalize for cytotoxicity, these Aβ results were divided by the MTT results and expressed as a percentage of the results from a drug-free control.

The test compounds were assayed for Aβ production inhibition activity in cells at 10 μg/mL using the test. The results presented in Table 1 are the mean and standard deviation of at least six replicate assays. $IC_{50}$ means the concentration of test compound in micromoles/liter required to inhibit Aβ production by 50%.

TABLE 1

| Aβ production inhibition activity in cells. | |
|---|---|
| Example | $IC_{50}$ (μM) |
| 1 | 3.7 |
| 2 | 3.1 |
| 3 | 2.7 |
| 4 | >20 |
| 5 | 4.4 |
| 6 | 4.7 |
| 7 | 4.5 |
| 8 | 2.6 |
| 9 | 4.9 |
| 10 | 7.1 |
| 11 | 12.5 |
| 12 | 3.9 |
| 13 | 1.7 |
| 14 | 12.1 |
| 15 | 3.7 |

TABLE 1-continued

| Aβ production inhibition activity in cells. | |
|---|---|
| Example | IC$_{50}$ (μM) |
| 16 | 11.8 |
| 17 | 9.7 |
| 18 | >20 |
| 19 | 13.8 |
| 20 | 4.4 |
| 21 | 8.3 |
| 22 | 4.3 |

The compounds of the present invention can be administered for prophylactic and/or therapeutic treatment of diseases related to the deposition of Aβ, such as Alzheimer's disease, Down's syndrome, and advanced aging of the brain. In therapeutic applications, the compounds are administered to a host already suffering from the disease. The compounds will be administered in an amount sufficient to inhibit further deposition of senile plaques. The specific dose of compound administered according to this invention to obtain therapeutic and/or prophylactic effects will, of course, be determined by the particular circumstances surrounding the case, including, for example, the compound administered, the route of administration, the condition being treated, the individual being treated and the like. A typical daily dose will contain a dosage level of from about 0.01 mg/kg to about 50 mg/kg of body weight of an active compound of this invention. Preferred daily doses generally will be from about 0.05 mg/kg to about 20 mg/kg, for example from about 0.1 mg/kg to about 10 mg/kg.

For prophylactic applications, the compounds of the present invention are administered to a warm-blooded mammal susceptible to Alzheimer's Disease or a βAP-related disease, but not already suffering from such disease. Such hosts may be identified by genetic screening and clinical analysis, as described in the medical literature. See e.g., Goate, (1991) Nature 349: 704–706. The compounds will be able to inhibit or prevent the formation of senile plaques at a symptomatically early stage, preferably preventing even the initial stages of the βamyloid disease.

The compounds can be administered by a variety of routes including oral, rectal, transdermal, subcutaneous, intravenous, intramuscular and intranasal. The compounds of the present invention are preferably formulated prior to administration.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

For example, a typical pharmaceutical composition for intramuscular injection would contain about one μg to one mg of the compound in from one to four milliliters of sterile buffered water. The typical pharmaceutical composition for intravenous infusion would contain about one to one hundred milligrams of the compound in from one hundred to five hundred milliliters of sterile Ringer's solution.

The pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The following Examples illustrate the invention.

In this specification, the following abbreviations have been used. THF refer to tetrahydrofuran, DMF refers to dimethylformamide, HPLC refers to high pressure liquid chromatography, DMAP refers to 4-dimethylaminopyridine, and DBU refers to 1,8-diazabicyclo[5,4,0]undec-7-ene.

General Procedures

In each of the following examples, one of the following three general procedures was used.

Procedure A. An amine (1 equivalent), isothiocyanate (1 equivalent), and 4-dimethylaminopyridine (1.1 equivalent) were dissolved in THF (2.5 ml/mmole) and stirred for 16 hr at room temperature under an atmosphere of nitrogen. The solution was concentrated in vacuo, ethyl acetate added, and washed twice with water. The organic layer was dried over sodium sulfate and condensed. The thiourea was purified by HPLC over silica gel eluted with 30% ethyl acetate/hexane.

Procedure B. An amine (1 equivalent), isothiocyanate (1 equivalent), and potassium carbonate (1 equivalent) were dissolved in THF (2.5 ml/mmole) and refluxed for 3 hr. The cooled solution was concentrated, ethyl acetate added, washed with water, dried over sodium sulfate and condensed. The product was purified by HPLC over silica gel eluted with ethyl acetate/hexane.

Procedure C. An amine (1 equivalent) and isothiocyanate (1 equivalent) were dissolved in THF (2.5 ml/mmole) and stirred at room temperature for 16 hr. The solution was concentrated, ethyl acetate added, washed with water, dried over sodium sulfate, and concentrated. The product was purified by HPLC over silica gel eluted with ethyl acetate/hexane.

Example 1

1-[4-(2-quinolyl)thiophenyl]-3-(4-chloro-3-trifluoromethyphenyl)thiourea 2-(4-aminophenylthio) quinoline (3.9 mmoles, 1.0 g) and 4-chloro-3-trifluoromethylphenylisothiocyanate (3.9 mmoles, 0.92 g) were reacted according to procedure A to yield 1.06 g, 56% of the title compound. Mass spec (FD) 490. Calculated for $C_{23}H_{15}ClF_3N_3S_2$: C, 56.38; H, 3.09, N, 8.58. Found: C, 56.60; H, 3.11; N, 8.42.

The necessary amine starting material was prepared as follows:

2-Chloroquinoline (0.04 moles, 6.54 g), 4-aminothiophenol (0.04 moles, 5.0 g) and potassium carbonate (0.04 moles, 5.52 g) were stirred at room temperature in 200 ml of ethanol for 18 hr. The reaction mixture was concentrated, ethyl acetate was added and the solution washed with water, dried over sodium sulfate and concentrated. The product was purified by HPLC over silica gel eluted with ethyl acetate/hexane to yield 2-(4-aminophenylthio)quinoline 4.0 g, 40%. Mass Spec (FD) 252. Calculated for $C_{15}H_{12}N_2S$: C, 71.40; H, 4.79, N, 11.10. Found: C, 71.11; H, 4.98 N, 11.20.

Example 2

1-[4-(4-ethoxycarbonyl-2-quinolylthio)phenyl]-3-(4-chloro-3-trifluoromethylphenyl)thiourea 2-(4-aminophenylthio)-4-ethoxycarbonylquinoline (6.0 moles, 2.0 g) and 4-chloro-3-trifluoromethylphenylisothiocyanate (6.0 mmoles, 1.4 g) were reacted according to procedure C to yield 3.0 g, 89% of the title compound. Mass Spec (FD) 561. Calculated for $C_{26}H_{19}ClF_3N_3O_2S_2$: C, 55.56; H, 3.41; N, 7.48. Found: C, 55.38 H, 3.38; N, 7.36.

The necessary amine stating material was prepared as follows:

2-Chloro-4-ethoxycarbonylquinoline (0.024 moles, 5.56 g), 4-aminothiophenol (0.024 moles, 3.0 g) and 4-dimethylaminopyridine (0.024 moles, 2.9 g) were stirred in 250 ml ethanol for 3 days. The reaction mixture was filtered, concentrated, ethyl acetate added, washed with water and dried over sodium sulfate. The solution was concentrated and the product purified by HPLC over silica gel eluted with 25% ethyl acetate/hexane to yield 2-(4-aminophenylthio)-4-ethoxycarbonylquinoline 2.8 g, 36%. Mass Spec (FD) 324. Calculated for $C_{18}H_{16}N_2O_2S$: C, 66.64; H, 4.97; N, 8.63. Found: C, 66.50; H, 5.00 N, 8.54.

Example 3

1-[4-(6-Chloro-2-quinolylthio)phenyl]-3-(4-chloro-3-trifluoromethylphenyl)thiourea 2-(4-Aminophenylthio)-6-chloroquinoline (2.9 mmoles, 0.83 g) and 4-chloro-3-trifluoromethylphenylisothiocyanate (3.2 mmoles, 0.76 g) were reacted according to procedure C to yield 0.78 g, 51% of the title compound. Mass Spec (FD) 524. Calculated for $C_{23}H_{14}ClF_3N_3S_2$: C, 52.68; H, 2.69; N, 8.01. Found: C, 52.66; H, 2.78; N, 7.91. M Pt 138°–139° C.

The necessary amine starting material was prepared as follows:

2,6-Dichloroquinoline (15.2 moles, 3.0 g), 4-aminothiophenol (15.2 moles, 1.9 g), and DMAP (15.2 moles, 1.85 g) were stirred at room temperature for 3 days. The solvent was removed, diluted with ethyl acetate, washed with water, dried over sodium sulfate and concentrated. The product was purified by HPLC over silica gel eluted with 25% ethyl acetate in hexane to yield 2-(4-aminophenylthio) -6-chloroquinoline 830 mg, 19%. Mass spec (FD) 286. Calculated for $C_{15}H_{11}ClN_2S$: C, 62.82 H, 3.87; N, 9.77. Found: C, 63.09; H, 3.94; N, 9.61.

Example 4

1-[4-(4-Phenyl-2-quinolylthio)phenyl]-3-(4-chloro-3-trifluoromethylphenyl)thiourea 2-(4-aminophenylthio)-4-phenylquinoline (3.0 moles, 1.0 g) and 4-chloro-3-trifluoromethylphenylisothiocyanate (3.3 mmoles, 0.79 g) were reacted according to procedure C to yield the title compound 1.03 g, 61%. Mass Spec (FD) 565. Calculated for $C_{29}H_{19}ClF_3N_3S_2$: C, 61.53; H, 3.38; N, 7.42. Found: C, 61.82; H, 3.63; N, 7.43.

The necessary amine starting material was prepared as follows:

2-Chloro-4-phenylquinoline (4.18 mmoles, 10.0 g), 4-aminothiophenol (41.8 mmoles, 5.2 g) and DMAP (41.8 mmoles, 5.0 g) were stirred in 200 ml ethanol and 50 ml THF for 3 days. The solution was concentrated, ethyl acetate added, washed with water, dried over sodium sulfate and the solvent removed. The product was purified by HPLC over silica gel eluted with 30% ethyl acetate in hexane to yield 2-(4-aminophenylthio)-4-phenylquinoline 6.2 g, 45%. Mass Spec (FD) 328. Calculated for $C_{21}H_{16}N_2S$: C, 76.80; H, 4.91 N, 8.53. Found: C, 77.04; H, 5.00; N, 8.55.

Example 5

1-[4-(6-Methoxy-2-quinolylthio)phenyl]-3-(4-chloro-3-trifluoromethylphenyl)thiourea 2-(4-aminophenylthio)-6-methoxyquinoline (15.0 moles, 4.2 g) and 4-chloro-3-trifluoromethylphenylisothiocyanate (15.0 mmoles, 3.6 g) were reacted according to procedure C to yield 5.6 g, 72% of the title compound. Mass Spec (FD) 519. Calculated for $C_{24}H_{17}ClF_3N_3OS_2$: C, 55.44; H, 3.30; N, 8.08. Found: C, 55.62; H, 3.43; N, 8.27.

The necessary amine starting material was prepared as follows:

2-Chloro-6-methoxyquinoline (52.0 mmoles, 10.0 g), 4-aminothiophenol (52.0 mmoles, 6.5 g) and dimethylaminopyridine (52.0 mmoles, 6.3 g) were stirred for 16 hr in 250 ml ethanol. The reaction was condensed and purified by HPLC over silica gel eluted with 25–30% ethyl acetate/hexane to yield 2-(4-aminophenylthio)-6-methoxyquinoline. 8.5 g, 58% product. Mass spec (FD) 282. Calculated for $C_{16}H_{14}N_2OS$: C, 68.06; H, 5.00, N, 9.92. Found: C, 68.04; H, 4.97; N, 10.02.

Example 6

1-[4-(4-Quinolylthio)phenyl]-3-(4-chloro-3-trifluoromethylphenyl)thiourea 4-(4-aminophenylthio)quinoline (3.9 moles, 1.0 g) and 4-chloro-3-trifluoromethylphenylisothiocyanate (3.9 moles, 0.92 g) were reacted according to procedure A to yield of the title compound 1.06 g, 56%. Mass spec (FD) 490. Calculated for $C_{23}H_{15}ClF_3N_3S_2$: C, 56.38; H, 3.09, N, 8.58. Found: C, 56.60; H, 3.11; N, 8.42.

The necessary amine starting material was prepared as follows:

a) 4-Chloroquinoline (32.3 mmoles, 5.2 g),4-nitrothiophenol (32.3 moles, 5.0 g) and potassium carbonate (32.3 moles, 4.46 g) were stirred at room temperature in 500 ml of ethanol for 16 hr. The reaction mixture was then concentrated, ethyl acetate was added and the solution washed with water, dried over sodium sulfate and concentrated. The product was purified by HPLC over silica gel eluted with 20–40% ethyl acetate/hexane to yield 4-(4-nitrophenylthio)quinoline 4.9 g, 54%. Mass Spec (FD) 282.

Calculated for $C_{15}H_{10}N_2O_2S$: C, 63.82 H, 3.57 N, 9.92. Found: C, 65.09; H, 3.81; N, 10.02.

b) 4-(4-nitrophenylthio)quinoline (17.0 mmoles, 4.9 g) was dissolved in 200 ml ethanol and hydrogenated over 5 g of 5% Pd/C at 40 psi for 1 hr at room temperature. The solution was filtered through celite and the solvent removed to yield 4-(4-aminophenylthio)quinoline 2.5 g, 58%. Mass spec (FD) 253. Calculated for $C_{15}H_{12}N_2S$: C, 71.40; H, 4.79, N, 11.10. Found: C, 1.12; H, 4.93 N, 10.88.

Example 7

1-[4-(7-Trifluoromethyl-4-quinolylthio)phenyl]-3-(4-chloro-3-trifluoromethylphenyl)thiourea 4-(4-aminophenylthio)-7-trifluoromethylquinoline (0.01 mole, 3.2 g) and 4-chloro-3-trifluoromethylphenylisothiocyanate (0.01 mole, 2.4 g) were reacted according to procedure C to yield the title compound 3.5 g, 63%. Mass Spec (FD) 557. Calculated for $C_{24}H_{14}ClF_6N_3S_2$: C, 51.66; H, 2.53; N, 7.53. Found: C, 51.92; H, 2.53; N, 7.46.

The necessary amine starting material was prepared as follows:

4-Chloro-7-trifluoromethylquinoline (0.043 moles, 10.0 g), 4-aminothiophenol (0.043 moles, 5.3 g) and 4-dimethylaminopyridine (0.04 moles, 4.9 g) were stirred in 250 ml ethanol for 3 days. The reaction mixture was filtered, concentrated, ethyl acetate added, washed with water and dried over sodium sulfate. The solution was concentrated and the product purified by HPLC over silica gel eluted with 25% ethyl acetate/hexane to yield 4-(4-aminophenylthio)-7-trifluoromethylquinoline 10.2 g, 74%. Mass Spec (FD) 320. Calculated for $C_{16}H_{11}F_3N_2S$: C, 59.99; H, 3.46; N, 8.74. Found: C, 60.08; H, 3.49; N, 8.77.

Example 8

1-[4-(2-Naphthylthio)phenyl]-3-(4-chloro-3-trifluoromethylphenyl)thiourea 2-(4-Aminophenylthio)naphthalene (4.2 mmoles, 1.06 g) and 4-chloro-3-trifluoromethylphenylisothiocyanate (4.2 mmoles, 0.93 g) were reacted according to procedure A to yield of the title compound 0.7 g, 34%. Mass Spec (FD) 489. Calculated for $C_{24}H_{16}ClF_3N_2S_2$: C,; H, N, Found: C,; H,; N,.

The necessary amine starting material was prepared as follows:

a) 2-Bromonaphthalene (0.08 moles, 16.6 g), 4-nitrothiophenol (0.08 moles, 12.4 g), potassium carbonate (0.1 moles, 13.4 g), copper bronze (6.0 g) and cuprous chloride (0.02 moles, 2.0 g) were heated under reflux for 4 days in 300 ml pyridine. The solution was filtered hot, concentrated, dissolved in ethyl acetate and washed thoroughly with 2N HCl and water. The solution was dried over sodium sulfate, concentrated and purified by HPLC over silica gel eluted with 5% ethyl acetate in hexane. The product was recrystallized from ethyl acetate and hexane to yield 2-(4-nitrophenylthio)naphthalene 2.6 g, 12% in the first crop. Mass spec. (FD) 281.

b) 2-(4-nitrophenylthio)naphthalene (9.2 moles, 2.6 g) was dissolved in 50 ml ethanol and 20 ml ethyl acetate and hydrogenated for 16 hrs at room temperature over 1.0 g 5% Pd/C. The solution was filtered through celite and concentrated to yield 2-(4-aminophenylthio)naphthalene 1.1 g, 47%.

Example 9

1-[4-(1-Naphthylthiophenyl)-3-(4-chloro-3-trifluoromethyphenyl)thiourea 1-(4-aminophenylthio)naphthalene (20 mmoles, 5.0 g) and 4-chloro-3-trifluoromethlphenylisothiocyanate (20 mmoles, 4.7 g) were reacted according to procedure C to yield of the title compound, 2.0 g, 20%. Mass spec (FD) 488. Calculated for $C_{24}H_{16}ClF_3N_2S_2$: C, 58.95; H, 3.30, N, 5.73 Found: C, 59.17; H, 3.51; N, 5.91.

The necessary amine starting material was prepared as follows:

a) 1-Bromonaphthalene (0.15 mole, 31.0 g),4-nitrothiophenol 0.11 mole, 17.0 g), potassium carbonate (0.15 moles, 20.7 g), copper bronze (0.3 moles, 18.9 g) and cuprous chloride (0.06 moles, 6.0 g) were refluxed in 500 ml pyridine for 3 days. The reaction was filtered while hot, and then concentrated. Ethyl acetate was added and the solution washed with water and 5N HCl, dried over sodium sulfate and concentrated. The product was purified twice by HPLC over silica gel eluted with 20% ethyl acetate/hexane followed by 5 ethyl acetate/hexane to yield 1-(4-nitrophenylthio)naphthalene 11.0 g, 26%. Mass Spec (FD) 282. Calculated for $C_{16}H_{11}NO_2S$: C, 68.31 H, 3.94, N, 4.98. Found: C, 68.52; H, 4.00; N, 4.77.

b) 1-(4—Nitrophenylthio)naphthalene (39.0 moles, 11.0 g) was dissolved in 200 ml ethyl acetate and hydrogenated over 8 g of 5% Pd/C at 40 psi for 1 hr at room temperature. The solution was filtered through celite and the solvent removed to yield 1-(4-aminophenylthio)naphthalene 9.0 g, 92%. Mass spec (FD) 251. Calculated for $C_{15}H_{17}NS$: C, 76.46; H, 5.21, N, 5.57 Found: C, 76.71; H, 5.39; N, 5.47.

Example 10

1-[4-(2-Benzimidazolylthio)phenyl]-3-(4-chloro-3-trifluoromethylphenyl)thiourea 2-(4—Nitrophenylthio)benzimidazole (5.0 mmoles, 1.37 g) was reduced in ethyl acetate over 1.37 g 5% Pd/C, filtered and condensed and then reacted with 4-chloro-3-trifluoromethylphenylisothiocyanate (5.0 moles, 1.0 g) according to procedure C to yield the title compound 0.12 g, 5% product. Mass Spec (FD) 479. Calculated for $C_{21}H_{14}ClF_3N_4S_2$: C, 52.66; H, 2.95; N, 11.70. Found: C, 52.85; H, 3.18; N, 10.47.

The necessary starting material was prepared as follows:

2-Chlorobenzimidazole (0.033 moles, 5.0 g), 4-nitrothiophenol (0.033 moles, 4.14 g), and DBU (0.033 moles, 5.0 g) in 200 ml ethanol were heated at 55° C. for 3 hr. The reaction was concentrated, ethyl acetate added, washed with water, dried over sodium sulfate and the solvent removed. The solid was slurred in hexane to yield 2-(4-nitrophenylthio)benzimidazole 1.37 g, 15%. Mass Spec (FD) 271. Calculated for $C_{13}H_8N_3O_2S$: C, 57.55; H, 3.34; N, 15.49. Found: C, 57.50; H, 5.54; N, 15.23.

Example 11

1-[4-(2-Benzoxazolylthio)phenyl]-3-(4-chloro-3-trifluoromethylphenyl)thiourea 2-(4-Aminophenylthio)benzoxazole (10.0 moles, 2.6 g) and 4-chloro-3-trifluoromethylphenylisothiocyanate (10.0 moles, 2.4 g) were reacted according to procedure A to yield of the title compound 1.6 g, 33%. Mass Spec (FD) 479. Calculated for $C_{21}H_{13}ClF_3N_3OS_2$: C, 52.56; H, 2.73; N, 8.75. Found: C, 52.47; H, 2.70; N, 8.48.

The necessary amine starting material was prepared as follows:

2-Chlorobenzoxazole (0.065 moles, 10.0 g), 4-aminothiophenol (0.065 moles, 8.1 g) and potassium carbonate (0.065 moles, 9.0 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 50% ethyl acetate in hexane to yield 2-(4-aminophenylthio) benzoxazole 12.5 g, 79%. Mass spec (FD) 243. Calculated for $C_{11}H_{10}N_2OS$: C, 64.44; H, 4.16; N, 11.56. Found: C, 64.53; H, 4.22; N, 11.58.

Example 12

1-[4-(2-Benzothiazolylthio)phenyl]-3-(4-chloro-3-trifluoromethylphenyl)thiourea 2-(4-Aminophenylthio)benzothiazole (10.0 moles, 2.6 g) and 4-chloro-3-trifluoromethylphenylisothiocyanate (10.0 moles, 2.4 g) were reacted according to procedure C to yield of the title compound, 1.5 g, 30%. Mass Spec (FD) 495. Calculated for $C_{21}H_{13}ClF_3N_3S_3$: C, 50.85 H, 2.64 N, 8.47. Found: C, 51.02; H, 2.71; N, 8.31.

The necessary amine starting material was prepared as follows:

2-Chlorobenzothiazole (0.06 moles, 10.1 g), 4-aminothiophenol (0.06 moles, 7.5 g) and potassium carbonate (0.06 moles, 8.3 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 40–60% ethyl acetate in hexane to yield 2-(4-aminophenylthio) benzothiazole 13.7 g, 88%. Mass spec (FD) 258. Calculated for $C_{11}H_{10}N_2S_2$: C, 60.44; H, 3.90; N, 10.84. Found: C, 60.63; H, 3.98; N, 11.01.

Example 13

1-[4-(5-Chloro-2-benzothiazolylthio)phenyl]-3-(4-chloro-3-trifluoromethylphenyl)thiourea 2-(4-aminophenylthio)-5-chlorobenzothiazole (5.5 moles, 1.6 g) and 4-chloro-3-trifluoromethylphenylisothiocyanate (5.5 moles, 1.3 g) were reacted according to procedure C to yield the title compound 0.7 g, 24%. Mass Spec (FD 529. Calculated for $C_{21}H_{12}C_{12}F_3N_3S_3$: C, 47.55; H, 2.28; N, 7.92. Found: C, 47.55; H, 3.32; N, 7.87.

The necessary amine starting material was prepared as follows:

2,5-Dichlorobenzothiazole (0.049 moles, 10.0 g), 4-aminothiophenol (0.049 moles, 6.1 g) and DMAP (0.049 moles, 6.0 g) were stirred for 3 days at room temperature in 250 ml ethanol, filtered, and concentrated. Ethyl acetate was added and the solution washed with water, dried over sodium sulfate and concentrated. The product was purified by HPLC over silica gel eluted with 25% ethyl acetate in hexane to yield 2-(4-aminophenylthio)-5-chlorobenzothiazole 3.2 g, 22%. Mass spec (FD) 292. Calculated for $C_{13}H_9ClN_2S_2$: C, 53.33; H, 3.10; N, 9.57. Found: C, 53.03; H, 3.30; N, 9.70.

Example 14

1-[4-(2-Quinolylsulfinyl)phenyl]-3-(4-chloro-3-trifluoromethylphenyl)thiourea 2-(4-aminophenylsulfinyl)quinoline (4.8 mmoles, 1.3 g) and 4-chloro-3-trifluoromethylphenylisocyanate (4.8 mmoles, 1.15 g) were reacted according to procedure C to yield the title compound 0.4 g, 16%. Mass Spec (FD) 505. Calculated for $C_{23}H_{15}ClF_3N_3OS_2$: C, 58.29; H, 3.19; N, 8.87. Found: C, 58.59; H, 3.60; N, 8.27.

The necessary starting material was prepared as follows:

a) 2-(4-Nitrophenylthio)quinoline (8.8 mmoles, 2.48 g) and m-chloroperbenzoic acid (8.8 mmoles, 3.37 g) were dissolved in 100 ml methylene chloride and stirred at room temperature for 18 hr. The solution was washed with water, dried over sodium sulfate, and concentrated. The product was purified by HPLC over silica gel eluted with 40% ethyl acetate/hexane to yield 4-nitrophenyl-2-quinolylsulfone 1.5 g, 54% and 4-nitrophenyl-2-quinolylsulfoxide 0.82 g, 31%. Sulfone: Mass spec (FD) 314. Calculated for $C_{15}H_{10}N_2O_4S$: C, 57.32; H, 3.21; N, 8.91. Found: C, 57.37; H, 3.18; N, 8.72. Sulfoxide: Mass spec (FD) 266. Calculated for $C_{15}H_{10}N_2O_3S$: C, 60.39; H, 3.38; N, 9.39. Found: C, 60.64; H, 3.18; N, 8.72.

b) 4—Nitrophenyl-2-quinolylsulfone (9.0 mmoles, 2.7 g) was dissolved in 200 ml ethanol and 75 ml DMF and was then hydrogenated over 2.2 g 5% Pd/C at room temperature for 3 hr. The reaction mixture was then filtered through celite and condensed to afford 2-(4-aminophenylsulfinyl) quinoline.

Example 15

1-[4-(2-Quinolylsulfonyl)phenyl]-3-(4-chloro-3-trifluoromethylphenyl)thiourea 2-(4-Aminophenylsulfonyl)quinoline (5.3 mmoles) and 4-chloro-3-trifluoromethylphenylisocyanate (5.8 mmoles, 1.38 g) were reacted according to procedure A to yield the title compound, 0.6 g, 2 %. Mass Spec (PD) 521. Calculated for $C_{23}H_{15}ClF_3N_3O_2S_2$: C, 52.93; H, 2.90; N, 8.05. Found: C, 53.21; H, 3.09; N, 8.25.

The necessary amine starting material was prepared as follows:

4-Nitrophenyl-2-quinolylsulfoxide (5.3 mmoles, 1.5 g) prepared as described in Example (14, step a), was dissolved in ethanol/ethyl acetate and hydrogenated over 1 g 5% Pd/C at room temperature for 3 hr. The reaction mixture was then filtered through celite and condensed to afford 2-(4-aminophenylsulfonyl)quinoline Mass spec (FD) 284. Calculated for $C_{15}H_{12}N_2O_2S$: C, 63.36; H, 4.25; N, 9.85. Found: C, 62.16; H, 4.25; N, 9.25.

Example 16

1-[4-(2-quinolylamino)phenyl]-3-(4-chloro-3-trifluoromethylphenyl)thiourea 2-(4-aminophenylamino)quinoline (5.0 moles, 1.15 g) and 4-chloro-3-trifluoromethylphenylisothiocyanate (5.0 moles, 1.20 g) were reacted according to procedure C of to yield the title compound 1.60 g, 68%. Mass Spec (FD) 473. Calculated for $C_{23}H_{16}C_1F_3N_4S$: C,; H,; N, Found: C,; H,; N,.

Example 17

1-[4-(2-Quinolyloxy)phenyl]-3-(4-chloro-3-trifluoromethylphenyl)thiourea 2-(4-Aminophenoxy)quinoline (2.4 moles, 0.56 g) and 4-chloro-3-trifluoromethylphenylisothiocyanate (2.4 moles, 0.57 g) were reacted according to procedure C to yield the title compound, 0.8 g, 70%. Mass Spec (FD) 473. Calculated for $C_{23}H_{15}ClF_3N_3OS$: C, 58.29; H, 3.19; N, 8.87. Found: C, 58.47; H, 3.48; N, 8.85.

The necessary amine starting material was prepared as follows:

a) 4-Nitrophenol (41 moles, 5.1 g) was dissolved in DMF (500 ml) and treated with sodium hydride (41 mmoles previously washed with hexane). After stirring at room temperature for 1 hr, 2-chloroquinoline (40 moles, 6.5 g) was added dropwise and stirred for 16 hr at room temperature followed by refluxing for 6 hr. Water was added to the cooled solution and the product was extracted with ethyl acetate. The ethyl acetate solution was washed with water, and 5N NaOH, dried over sodium sulfate and concentrated. The product was purified by HPLC over silica gel eluted with ethyl acetate/hexane to yield 2-(4-nitrophenoxy) quinoline. 3.1 mmoles, 8%. Mass Spec (FD) 266. Calcd for $C_{15}H_{10}N_2O_3$: C, 67.45; H, 3.84; N, 10.40. Found: C, 65.84; H, 3.88; N, 8.47.

b) 2-(4-Nitrophenoxy)quinoline (3 mmoles, 0.82 g) was dissolved in 100 ml ethyl acetate and hydrogenated over 2.0 g 5% Pd/C at room temperature for 1 hr. The solution was filtered through cellulose and concentrated to yield 2-(4-aminophenoxy)quinoline 0.58, 82%. Mass Spec (FD) 236. Calculated for $C_{15}H_{12}N_2O$: C, 76.25; H, 5.12, N, 11.86. Found: C, 75.97; H, 5.37; N, 11.83.

Example 18

1-[4-(2-Quinolylthio)phenyl]-3-(4-chloro-3-trifluoromethylphenyl]urea 2-(4-Aminophenylthio)quinoline (3.9 moles, 1.0 g) and 4-chloro-3-trifluoromethylphenylisocyanate (3.9 moles, 0.85 g) were reacted according to procedure A to yield the title compound, 0.8 g, 43%. Mass Spec (FD) 463. Calculated for $C_{23}H_{15}ClF_3N_3OS$: C, 58.29; H, 3.19; N, 8.87. Found: C, 58.56; H, 3.43; N, 9.02. M Pt 194°–195 ° C.

Example 19

1-[4-(2-Quinolylthio)phenyl]-3-(3,4-dichlorophenyl) thiourea 2-(4-Aminophenylthio)quinoline (11.9 moles, 3.0 g) and 3,4-dichlorophenylisothiocyanate (11.9 mmoles, 2.42 g) were reacted according to procedure B to yield the title compound, 360 mg, 6.6%. Mass Spec (FD) 455. Calculated for $C_{22}H_{15}Cl_2N_3S_2$: C, 57.90 H, 3.31; N, 9.21. Found: C, 57.86; H, 3.53; N, 9.07. m.p. 125°–126°.

The necessary amine starting material was prepared as follows:

a) 2-Chloroquinoline (0.12 moles, 20.0 g), 4-nitrothiophenol (0.13 moles, 20.8 g), and potassium carbonate (0.13 moles, 18.5 g) were dissolved in 800 ml ethanol and stirred at room temperature for 1.5 hr. The mixture was filtered and the solid washed with ethanol. The solid was dissolved with ethyl acetate, washed with water, dried over sodium sulfate and concentrated to yield 2-(4-nitrophenylthio)quinoline 26.0 g, 77%. Mass Spec (FD) 282. Calculated for $C_{15}H_{10}N_2O_2S$: C, 63.82, H 3.57; N, 9.92. Found: C, 63.55, H 3.59; N, 9.71.

b) 2-(4-Nitrophenylthio)quinoline (0.42 moles, 12.0 g) was hydrogenated in 300 ml DMF over 5.0 g Pd/C for 3 hr at room temperature. The solution was filtered through celite and concentrated. The product was triturated with ether and hexane to yield 2-(4-aminophenylthio)quinoline 10.0 g, 93%.

Example 20

3-[4-(6-phenyl-3-pyridazylthio)phenyl]-3-(4-chloro-3-trifluoromethylphenyl)thiourea 3-(4-aminophenylthio)-6-phenylpyridazine (7.0 mmoles, 2.0 g) and 4-chloro-3-trifluoromethylphenylisothiocyanate (7.0 mmoles, 1.66 g) were reacted according to procedure C to yield of the title compound 2.5 g, 69%. Mass Spec (FD) 516. Calculated for $C_{24}H_{16}ClF_3N_4O_2S_2$: C, 55.76; H, 3.12; N, 10.84. Found: C, 55.98 H, 3.19; N, 10.78.

The necessary amine starting material was prepared as follows:

3-Chloro-6-phenylpyridazine (0.026 moles, 5.0 g), 4-aminothiophenol (0.026 moles, 3.3 g) and potassium carbonate (0.026 moles, 3.6 g) were stirred in 250 ml ethanol for 3 days. The reaction was filtered, concentrated, ethyl acetate added, washed with water and dried over sodium sulfate. The solution was concentrated and the product purified by HPLC over silica gel eluted with 50% ethyl acetate/hexane to yield 3-(4-aminophenylthio)-6-phenylpyridazine 6.0 g, 83%. Mass Spec (FD) 279. Calculated for $C_{16}H_{13}N_3S$: C, 68.79; H, 4.69; N, 15.04. Found: C, 68.87; H, 4.43 N, 15.31.

Example 21

1-[4-(2-pyridylthio)phenyl-3-(4-chloro-3-trifluoromethylphenyl)thiourea 2-(4-Aminophenylthio)pyridine (6.0 mmoles, 1.2 g) and 4-chloro-3-trifluoromethylphenylisothiocyanate (6.0 mmoles, 1.4 g) were reacted according to procedure C to yield the title compound, 1.9 g, 72%. Mass spec (FD) 439. Calculated for $C_{19}H_{13}ClF_3N_3S_2$: C, 51.88; H, 2.98, N, 9.55 Found: C, 51.99; H, 3.15; N, 9.63.

The necessary amine starting material was prepared as follows:

4-Aminothiophenol (0.065 moles, 8.1 g) in 275 ml DMF was stirred at room temperature for 1 hr with sodium hydride (0.065 moles previously washed with hexane). 2-Chloropyridine (0.06 moles, 6.8 g) was added and the reaction mixture was stirred for 6 hr. An additional 5.2 g of 4-aminothiophenol was added and the reaction stirred at room temperature for 16 hr. Water was added and the product extracted with ethyl acetate. The solution was washed thoroughly with water, dried over sodium sulfate and concentrated. The product was purified by HPLC over silica gel eluted with 30% ethyl acetate/hexane to yield 2-(4-aminophenylthio)pyridine 1.2 g, 10%. Mass spec (FD) 202. Calculated for $C_{11}H_{10}N_2S$: C, 65.32; H, 4.98, N, 13.85 Found: C, 65.23; H, 5.09; N, 13.63.

Example 22

1-[4-(5-Nitroquinol-6-ylthio)phenyl-3-(4-chloro-3-trifluoromethylphenyl)thiourea 5-nitro-6-(4-aminophenylthio)quinoline (1.7 mmoles, 0.40 g) and 4-chloro-3-trifluoromethylphenylisothiocyanate (1.7 mmoles, 0.47 g) were reacted according to procedure C to yield the title compound, 0.78 g, 86% product. Mass spec (FD) 534. Calculated for $C_{23}H_{14}ClF_3N_4O_2S_2$: C, 51.64; H, 2.64, N, 10.47 Found: C, 51.84; H, 2.73; N, 10.43.

Example 23

The following illustrates pharmaceutical compositions comprising a compound of formula I as the active ingredient.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| | |
|---|---|
| Active Ingredient | 225 mg |
| | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| Active Ingredient | 100 mg |
| Mannitol | 100 mg |
| 5 N Sodium hydroxide | 200 ml |
| Purified water to total | 5 ml |

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion

We claim:

1. A compound of the formula

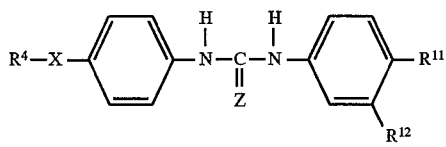

in which

Z is O or S;

$R^{11}$ is a halogen atom;

$R^{12}$ is a halogen atom or a trifluoromethyl group;

X is S, SO, $SO_2$, O or NH; and $R^4$ is naphthyl, quinolinyl, benzimidazolyl, pyridyl, pyridazinyl, benzoxazolyl or benzothiazolyl, unsubstituted or substituted by one or two substituents selected from a halogen atom, (1–4C)alkyl, (1–4C)alkoxy, nitro, (1–4C)alkoxycarbonyl, halo(1–4C)alkyl, and phenyl;

with the proviso that when $R^4$ is pyridyl or pyridazinyl X must be S, SO, $SO_2$ or NH;

or a pharmaceutically acceptable salt thereof.

2. A compound as claimed in claim 1, in which $R^4$ is unsubstituted or substituted naphth-1-yl, naphth-2-yl, quinolin-2-yl, quinolin-4-yl, quinolin-6-yl, benzimidazol-2-yl, benzoxazol-2-yl, benzothiazol-2-yl, pyridin-2-yl or pyridazin-3-yl.

3. A compound as claim in claim 1, in which $R^{11}$ is chlorine and $R^{12}$ is chlorine or trifluoromethyl.

4. A compound as claimed in claim 1, in which $R^4$ is naphth-1-yl, naphth-2-yl, quinolin-2-yl, 6-chloroquinolin-2-yl, 6-methoxyquinolin-2-yl, 5-nitroquinolin-6-yl, 4-ethoxycarbonylquinolin-2-yl, 4-phenylquinolin-2-yl, 7-trifluoromethylquinolin-4-yl, quinolin-4-yl, benzimidazol-2-yl, benzoxazol-2-yl, benzothiazol-2-yl, 5-chloro-benzothiazol-2-yl, 6-phenylpyrazin-3-yl or pyridin-2-yl.

5. A compound as claimed in claim 1, in which X is S.
6. A compound as claim in claim 1, in which Z is S.
7. A compound as claimed in claim 1, in which Z is O or S;

$R^{11}$ is a chlorine atom;

$R^{12}$ is a chlorine atom or a trifluoromethyl group;

X is S, $SO_2$, O or NH; and $R^4$ is naphth-1-yl, naphth-2-yl, quinolin-2-yl, 6-chloroquinolin-2-yl, 6-methoxyquinolin-2-yl, 5-nitroquinolin-6-yl, 4-ethoxycarbonylquinolin-2-yl, 4-phenylquinolin-2-yl, 7-trifluoromethylquinolin-4-yl, quinolin-4-yl, benzimidazol-2-yl, benzoxazol-2-yl, benzothiazol-2-yl, 5-chlorobenzothiazol-2-yl, 6-phenylpyrazin-3-yl or pyridin-2-yl.

8. A compound as claimed in claim 1, which is 1-[4-(2-quinolyl) thiophenyl]-3-(4-chloro-3-trifluoromethylphenyl) thiourea.

9. A pharmaceutical composition, which comprises a compound as defined in claim 1 and a pharmaceutically acceptable diluent or carrier.

10. A pharmaceutical composition which comprises a compound of the formula

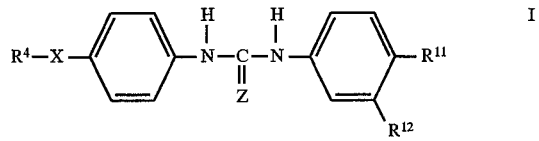

in which

Z is O or S;

$R^{11}$ is a halogen atom;

$R^{12}$ is a halogen atom or a trifluoromethyl group;

X is S, SO, $SO_2$, O or NH; and $R^4$ is naphthyl, quinolinyl, benzimidazolyl, pyridyl, pyridazinyl, benzoxazolyl or benzothiazolyl, unsubstituted or substituted by one or two substituents selected from a halogen atom, (1–4C)alkyl, (1–4C)alkoxy, nitro, 1–4C)alkoxycarbonyl, halo(1–4C)alkyl, and phenyl;

or a pharmaceutically acceptable salt thereof and a pharmaceutically acceptable diluent or carrier.

11. A method of inhibiting the production of Aβ peptide in a biological system, which comprises administering an effective amount of a compound as defined in claim 10.

12. A method of inhibiting the accumulation of Aβ peptide in senile plaques in a warm blooded mammal, which comprises administering an effective amount of a compound as defined in claim 10.

* * * * *